United States Patent [19]

Brennan et al.

[11] 4,078,990

[45] Mar. 14, 1978

[54] MANUFACTURE OF LOWER AROMATIC COMPOUNDS

[75] Inventors: James A. Brennan, Cherry Hill; Roger A. Morrison, West Deptford, both of N.J.

[73] Assignee: Mobil Oil Corporation, New York, N.Y.

[21] Appl. No.: 774,304

[22] Filed: Mar. 4, 1977

[51] Int. Cl.² .......................... C10G 35/06; C07C 3/58
[52] U.S. Cl. .................................. 208/64; 260/672 T
[58] Field of Search ....................... 208/64; 260/672 T

[56] References Cited

U.S. PATENT DOCUMENTS

| | | |
|---|---|---|
| 3,281,483 | 10/1966 | Benesi et al. ............... 260/672 T |
| 3,578,723 | 5/1971 | Bowes et al. ............... 260/672 T |
| 3,945,913 | 3/1976 | Brennan et al. ............... 208/64 |

*Primary Examiner*—C. Davis
*Attorney, Agent, or Firm*—Charles A. Huggett; Michael G. Gilman

[57] ABSTRACT

Certain acidic heterogeneous catalysts produce large yields of benzene, toluene and xylene from alkyl aromatics of at least nine carbon atoms by a mechanism different from the classical disproportionation reaction characteristic of acid catalysts. Typically, aromatic mixtures so derived from such stocks have unusually low content of ethyl benzene, thus greatly simplifying separation of xylene isomers.

22 Claims, 3 Drawing Figures

MANUFACTURE OF LOWER AROMATIC COMPOUNDS

BACKGROUND OF THE INVENTION

Of the aromatic compounds used in industry, benzene, toluene and xylenes are of outstanding importance on a volume basis. That mix of compounds, often designated BTX for convenience, is derived primarily from such aromatic naphthas as petroleum reformates and pyrolysis gasolines. The former result from processing petroleum naphthas over a catalyst such as platinum on alumina at temperatures which favor dehydrogenation of naphthenes. Pyrolysis gasolines are liquid products resulting from mild hydrogenation (to convert diolefins to olefins without hydrogenation of aromatic rings) of the naphtha fraction from steam cracking of hydrocarbons to manufacture ethylene, propylene, etc.

Regardless of aromatic naphtha source, it is usual practice to extract the liquid hydrocarbon with a solvent highly selective for aromatics to obtain an aromatic mixture of the benzene and alkylated benzenes present in the aromatic naphtha. That aromatic extract may then be distilled to separate benzene, toluene and $C_8$ aromatics from higher boiling compounds in the extract. The benzene and toluene are recovered in high purity but the $C_8$ fraction, containing valuable para xylene, is a mixture of the three xylene isomers with ethyl benzene. Techniques are known for separating p-xylene by fractional crystallization with isomerization of the other two isomers for recycle in a loop to the p-xylene separation. That operation is hampered by the presence of ethyl benzene (EB). However, a widely used xylene isomerization technique, "Octafining" can be applied. Octafining by passing the $C_8$ aromatics lean in p-xylene and mixed with hydrogen over platinum on silica-alumina not only isomerizes xylenes but also converts ethyl benzene, thus preventing build-up of EB in the separation-isomerization loop.

The manner of producing p-xylene by a loop including Octafining can be understood by consideration of a typical charge from reforming petroleum naphtha. The $C_8$ aromatics in such mixtures and their properties are:

|  | Freezing Point ° F. | Boiling Point ° F. | Density Lbs./U.S. Gal. |
|---|---|---|---|
| Ethyl benzene | −139.0 | 277.1 | 7.26 |
| P-xylene | 55.9 | 281.0 | 7.21 |
| M-xylene | −54.2 | 282.4 | 7.23 |
| O-xylene | −13.3 | 292.0 | 7.37 |

Principal sources are catalytically reformed naphthas and pyrolysis distillates. The $C_8$ aromatic fractions from these sources vary quite widely in composition but will usualy be in the range 10 to 32 wt.% ethyl benzene with the balance, xylenes, being divided approximately 50 wt.% meta, and 25 wt.% each of para and ortho.

In turn, calculated thermodynamic equilibra for the $C_8$ aromatic isomers at Octafining conditions are:

| Temperature | 850° F. |
|---|---|
| Wt. % Ethyl benzene | 8.5 |
| Wt. % para xylene | 22.0 |
| Wt. % meta xylene | 48.0 |
| Wt. % ortho xylene | 21.5 |
| TOTAL | 100.0 |

An increase in temperature of 50° F. will increase the quilibrium concentration of ethyl benzene by about 1 wt.%, ortho xylene is not changed and para and meta xylenes are both decreased by about 0.5 wt.%.

Individual isomer products may be separated from the naturally occurring mixtures by appropriate physical methods. Ethyl benzene may be separated by fractional distillation although this is a costly operation. Ortho xylene may be separated by fractional distillation and is so produced commercially. Para xylene is separated from the mixed isomers by fractional crystallization.

As commercial use of para and ortho xylene has increased there has been interest in isomerizing the other $C_8$ aromatics toward an equilibrium mix and thus increasing yields of the desired xylenes.

Octafining process operates in conjunction with the product xylene or xylenes separation processes. A virgin $C_8$ aromatics mixture is fed to such a processing combination in which the residual isomers emerging from the product separation steps are then charged to the isomerizer unit and the effluent isomerizate $C_8$ aromatics are recycled to the product separation steps. The composition of isomerizer feed is then a function of the virgin $C_8$ aromatic feed, the product separation unit performance, and the isomerizer performance.

The isomerizer unit itself is most simply described as a single reactor catalytic reformer. As in reforming, the catalyst contains a small amount of platinum and the reaction is carried out in a hydrogen atmosphere.

Octafiner unit designs recommended by licensors of Octafining usually lie within these specification ranges:

| Process Conditions | |
|---|---|
| Reactor Pressure | 175 to 225 PSIG |
| Reactor Inlet Temperature Range | 830 – 900° F. |
| Heat of Reaction | Nil |
| Liquid Hourly Space Velocity | 0.6 to 1.6 Vol/Vol/Hr. |
| Number of Reactors, Downflow | 1 |
| Catalyst Bed Depth, Feet | 11 to 15 |
| Catalyst Density, Lb/Cu. Ft. | 38 |
| Recycle Circulation, Mols Hydrogen/Mol Hydrocarbon Feed | 7.0 to 14.0 |
| Maximum Catalyst Pressure Drop, PSI | 20 |

It will be apparent that under recommended design conditions, a considerable volume of hydrogen is introduced with the $C_8$ aromatics. In order to increase throughput, there is great incentive to reduce hydrogen circulation with consequent increase in aging rate of the catalyst. Aging of catalyst occurs through deposition of carbonaceous materials on the catalyst with need to regenerate by burning off the coke when the activity of the catalyst has decreased to an undesirable level. Typically the recommended design operation will be started up at about 850° F. with reaction temperature being increased as needed to maintain desired level of isomerization until reaction temperature reaches about 900° F. At that point the isomerization is taken off stream and regenerated by burning of the coke deposit.

A typical charge to the isomerizing reactor may contain 17 wt.% ethyl benzene, 65 wt.% m-xylene, 11 wt.% p-xylene and 7 wt.% o-xylene. The thermodynamic equilibrium varies slightly with temperature. The objective in the isomerization reactor is to bring the charge as near to theoretical equilibrium concentrations as may be feasible consistent with reaction times which do not give extensive cracking and disproportionation.

Ethyl benzene reacts through ethyl cyclohexane to dimethyl cyclohexanes which in turn equilibrate to xylenes. Competing reactions are disproportionation of ethyl benzene to benzene and diethyl benzene, hydrocracking of ethyl benzene to ethane and benzene and hydrocracking of the alkyl cyclohexanes.

The rate of ethyl benzene approach to equilibrium concentration in a $C_8$ aromatic mixture is related to effective contact time. Hydrogen partial pressure has a very significant effect on ethyl benzene approach to equilibrium. Temperature change within the range of Octafining conditions (830° to 900° F.) has but a very small effect on ethyl benzene approach to equilibrium.

Concurrent loss of ethyl benzene to other molecular weight products relate to % approach to equilibrium. Products formed from ethyl benzene include $C_6+$ naphthenes, benzene from cracking, benzene and $C_{10}$ aromatics from disproportionation, and total loss to other than $C_8$ molecular weight. $C_5$ and lighter hydrocarbon by-products are also formed.

The three xylenes isomerize much more selectively than does ethyl benzene, but they do exhibit different rates of isomerization and hence, with different feed composition situations the rates of approach to equilibrium vary considerably.

Loss of xylenes to other molecular weight products varies with contact time. By-products include naphthenes, toluene, $C_9$ aromatics and $C_5$ and lighter hydrocracking products.

Ethyl benzene has been found responsible for a relatively rapid decline in catalyst activity and this effect is proportional to its concentration in a $C_8$ aromatic feed mixture. It has been possible then to relate catalyst stability (or loss in activity) to feed composition (ethyl benzene content and hydrogen recycle ratio) so that for any $C_8$ aromatic feed, desired xylene products can be made with a selected suitably long catalyst use cycle.

Because of its behavior in the loop for manufacture of p-xylene, or other xylene isomer, ethyl benzene is undesirable in the feed but is tolerated because of the great expense of removal from mixed $C_8$ aromatics. Streams substantially free of ethyl benzene are available from such processes as transalkylation of aromatics having only methyl substituents. Thus toluene can be reacted with itself (the specific transalkylation reaction sometimes called "disproportionation") or toluene may be reacted with tri-methyl benzene in known manner. Improved catalysts for these reactions are described in U.S. Pat. No. 3,790,471, granted Feb. 5, 1974.

The transalkylation reactions provide means for utilizing the higher boiling aromatics separated in preparing BTX from reformates. Thus toluene may be reacted with trimethyl benzenes to produce xylenes. They are also useful in handling high boiling aromatics formed by side reactions in such processes as isomerization of xylenes.

These conventional techniques make BTX available for the chemical industry by removing light aromatics from the "gasoline pool" of the petroleum fuels industry. This is an unfortunate result, particularly under present trends for improvement of the atmosphere by steps to reduce hydrocarbon and lead emissions from internal combustion engines used to power automotive equipment.

By far the greatest amount of unburned hydrocarbon emissions from cars occurs during cold starts while the engine is operating below design temperature. It has been contended that a more volatile motor fuel will reduce such emissions during the warm-up period. In addition, the statutory requirements for reduction and ultimate discontinuance of alkyl lead anti-knock agents require that octane number specifications be met by higher content of high octane number hydrocarbons in the motor fuel.

The net effect of the trends in motor fuel composition for environmental purposes is increased need for light aromatics to provide high volatility and octane number for motor gasoline. Present practices for supply of BTX to the chemical industry run counter to the needs of motor fuel supply by removing the needed light aromatics from availability for gasoline blending.

It is known that acid zeolites are very effective for disproportionation of alkyl aromatic compounds. See Frilette et al. U.S. Pat. No. 3,506,731, Wallace et al. U.S. Pat. No. 3,808,284 and Inoue et al. U.S. Pat. No. 3,671,602. The latter has shown that heavier aromatics, e.g. tri-methyl benzenes may be disproportionated to BTX and $C_{10}^+$ aromatics. The problem with that course is that a substantial portion of the product is $C_{10}^+$ aromatics which boil >350°F., which is at the upper limit or above the gasoline range and has little or no value as chemicals.

It has been proposed to subject the heavier alkyl aromatics to catalytic dealkylation for that purpose. See, for example, Japanese 7 6029-131 as abstracted at Chemical Products section of API Patent Alert dated Nov. 22, 1976. Alternatively, the heavier alkyl aromatics may be completely dealkylated to yield benzene from which a variety of alkyl aromatics can be prepared.

It is apparent that need exists for a process which will satisfy the BTX demand without removing those compounds from gasoline blending stocks.

SUMMARY OF THE INVENTION

That need is met by the process of our prior U.S. Pat. No. 3,945,913 of Mar. 23, 1976 which, in its preferred embodiments comprises modification of petroleum refinery operation to remove the $C_9^+$ fraction of catalytic reformate for processing to BTX and using the lighter fraction of reformate in blending of motor fuel. By this means, high front end volatility and octane number are preserved for gasoline. In its broader aspect, that invention contemplates manufacture of BTX from alkyl benzenes of nine or more carbon atoms by processing over unique acid zeolite catalysts in the presence of hydrogen.

The high boiling aromatics, nine carbon atoms or more, are convertible to BTX over catalyst characterized by acid zeolite of the ZSM-5 type, zeolite ZSM-12 or zeolite ZSM-21. That the reaction is not simply dealkylation is clear from the fact that the aliphatic by-products include large amounts of paraffins having more carbon atoms than the alkyl side chains of the aromatics charged. The process of the patent is conducted at 550° to 1000° F. under pressures of 100 to 2000 pounds per square inch in the presence of 0.5 to 10 mols of hydrogen per mol of hydrocarbon charge. Since the preferred catalysts are composites of zeolite with relatively inert porous matrix, the space velocity is best related to weight of active zeolite in the catalyst. Weight hourly space velocities on that basis between 0.5 and 200 are suitable.

The charge for the preferred embodiment of producing BTX (while making gasoline having good front end volatility, high octane number and low heavy end content) is here designated "$C_9^+$reformate". As is well known in the petroleum refining art, this does not normally define a fraction free of lighter material. Petroleum refinery fractionation is relatively imprecise, being designed to produce distillate and bottom cuts of desired boiling range. The invention is intended for use in conventional equipment of petroleum refineries and therefore contemplates "sloppy" fractionation. The term "$C_9^+$ reformate" as used herein means a fraction which contains most of the $C_9$ aromatics in the reformate and substantially all of the heavier aromatics present in the reformate. In general, the $C_9^+$ reformate will contain 20% by weight or less of xylenes.

It is a characteristic feature of catalytic reforming that the heavy end contempleted for use in this invention is very low in aliphatic components. A very high proportion of the alkyl carbon atom content is constituted by alkyl substituents on aromatic rings. To a major extent, those side chains have been reduced to methyl groups. A moderate amount of ethyl groups are present and a few propyl and butyl groups are also seen in a typical heavy reformate. Longer alkyl chains are so minor that they can be disregarded. A principal reaction appears to be rearrangement and removal of methyl groups and removal of those few higher alkyl side chains present in the charge.

The course of the conversion necessarily results in production of aliphatic hydrocarbons in reducing higher alkyl aromatics to BTX. Surprisingly, the alkyl compounds in the reaction product are predominantly longer chains that the substituents on the rings in the charge. This characteristic of the reaction is extremely valuable in a process conducted under hydrogen pressure as is the process of the patent and the process of this invention. A molar excess of hydrogen is preferred. In order to achieve maximum economy of operation, hydrogen is separated from the product and recycled to the inlet of the reactor. Methane, being difficult to separate from hydrogen without expensive cryogenic equipment, tends to build up in the recycle hydrogen and requires that a portion of the recycle stream be withdrawn to maintain adequate hydrogen purity. That withdrawn stream, as in other processes using hydrogen, e.g. catalytic reforming, is of value only for fuel. Such degradation of hydrogen value is obviated in large measure by the process of our cited patent because of the low methane concentration in the reactor effluent.

Although $C_9^+$ reformate is the preferred commercial feedstock for this process, it is obvious that other sources of $C_9^+$ aromatic concentrates comprised primarily of $C_1$ and $C_2$ alkylbenzenes will serve as well. One such source is pyrolysis gasoline from the production of ethylene.

It is noted further that the yield of aliphatics boiling in the BTX range is nil, thus providing high purity aromatic products.

As study proceeded with respect to the process of our patent, examination of the reaction kinetics provided an explanation of the unique chemistry involved. It is found that dealkylation of alkyl side chains having two or more carbon atoms is extremely rapid, proceeding to near completion in the shallow portion of the catalyst bed first contacted by the reactants. For that reason, the mixture brought into contact with the major portion of the catalyst is constituted by methyl benzene diluted by alkanes of two or more carbon atoms. The reaction occuring in that major portion of the bed is therefore transalkylation (including disproportionation) of methyl benzenes to approach the thermodynamic equilibrium.

From these findings, it was reasoned that the reaction should proceed with any acid heterogeneous catalyst since these are known to have activity for hydrodealkylation and for transalkylation.

Upon testing that hypothesis, it was found that the unique course of the reaction does indeed take place with solid, porous catalyst having acid activity. This application is directed to that extension of the novel process to include use of such acid catalysts other than the particular zeolites described in our said patent. Typically, the catalysts of the present invention differ from those of our patent in having pores of such size that hydrocarbon molecules of the sizes found in reformates freely pass therethrough at about the same rate of diffusion, a property hereinafter defined as "constraint index" not greater than unity. The catalysts iof this application thus include such crystalline aluminosilicate zeolites as X, Y, mordenite, beta, as well as the amorphous acid catalysts. The amorphous acid catalysts of greater present importance in commercial use are composites of silica and alumina prepared as co-gels, co-precipitates or milled mixtures of silica and alumina gels or precipitates. Alternatively, these mixtures may be prepared by precipitating one oxide on a gel or precipitate of the other. Other acid porous oxides are also contemplated such as silica-zirconia, silica-thoria, silica-magnesia and the like.

BRIEF DESCRIPTION OF THE DRAWINGS

Preferred embodiments of the invention are illustrated by the annexed drawings wherein.

Figure 1:
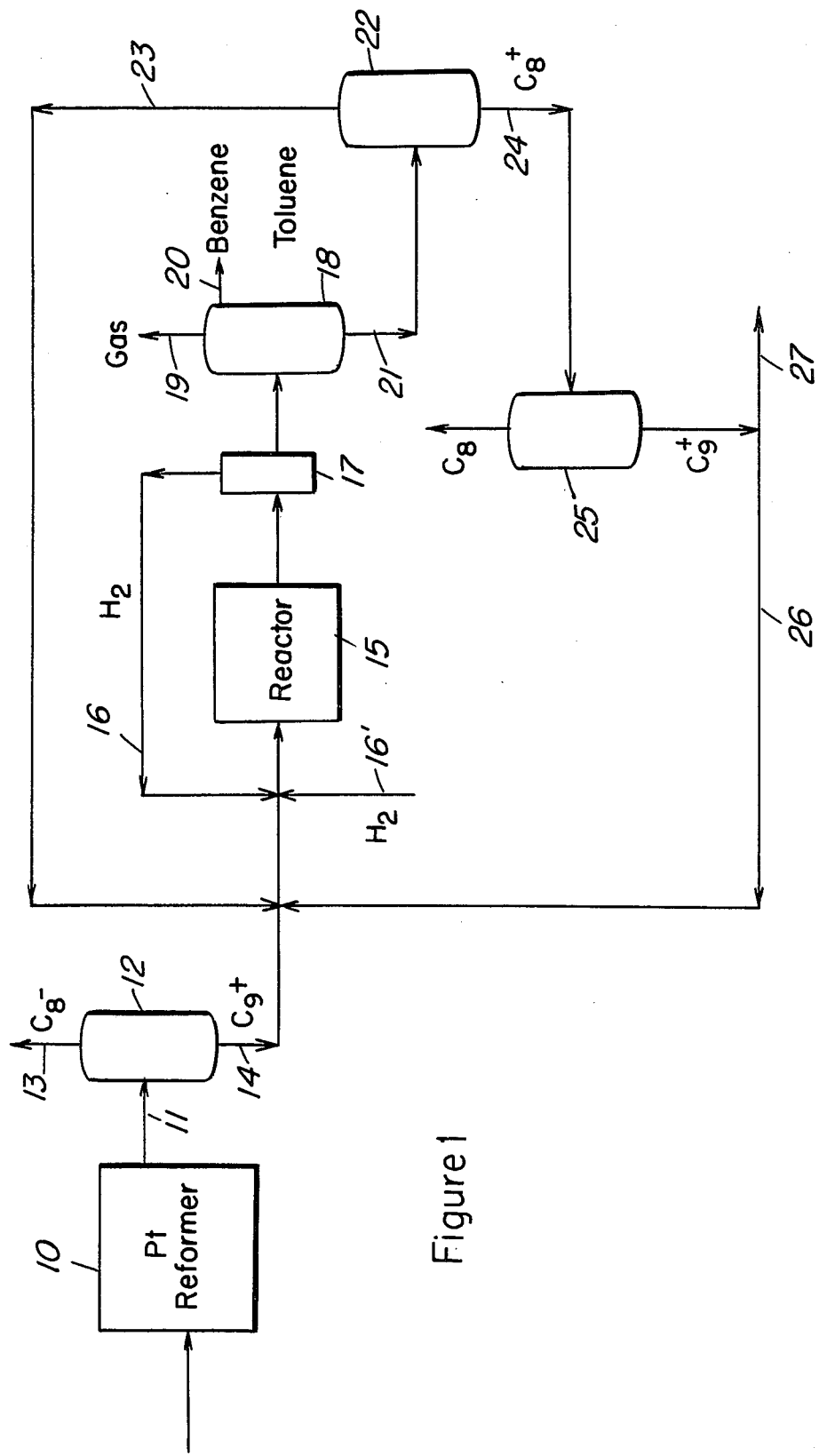
FIG. 1 is a flow sheet of combined motor fuel manufacture and production of BTX according to the invention.

3A represents conventional practice in manufacture of BTX;

3B illustrates application of the present invention for maximum BTX; and 3C is a simplification of FIG. 1.

DESCRIPTION OF SPECIFIC EMBODIMENTS

As stated above, the catalysts employed are porous solids having acidic surface characteristics and demonstrating a "constraint index" not greater than 1.

A simple determination of the "constraint index" may be made by passing continuously a mixture of an equal weight of normal hexane and 3-methylpentane over a small sample, approximately 1 gram or less, of catalyst at atmospheric pressure according to the following procedure. A sample of the catalyst, in the form of pellets or extrudate, is crushed to a particle size of about that of coarse sand and mounted in a glass tube. Prior to testing, the catalyst is treated with a stream of air at 1000° F. for at least 15 minutes. The catalyst is then flushed with helium and the temperature adjusted between 550° F. and 950° F. to give an overall conversion between 10% and 60%. The mixture of hydrocarbons is passed at 1 liquid hourly space velocity (i.e., 1 volume of liquid hydrocarbon per volume of catalyst per hour) over the catalyst with a helium dilution to give a helium to total hydrocarbon mole ratio of 4:1. After 20 minutes on stream, a sample of the effluent is taken and analyzed, most conveniently by gas chromatography, to determine the fraction remaining unchanged for each of the two hydrocarbons.

The "constraint index" is calculated as follows:

$$\text{Constraint Index} = \frac{\log_{10}(\text{fraction of n-hexane remaining})}{\log_{10}(\text{fraction of 3-methylpentane remaining})}$$

The constraint index approximates the ratio of the cracking rate constants for the two hydrocarbons. Catalysts suitable for the present invention are those having a constraint index not greater than unity. Constraint Index (CI) values for some typical catalysts are:

| CAS | C.I. |
|---|---|
| ZSM-5 | 8.3 |
| ZSM-11 | 8.7 |
| ZSM-12 | 2 |
| ZSM-38 | 2 |
| ZSM-35 | 4.5 |
| TMA Offretite | 3.7 |
| Beta | 0.6 |
| ZSM-4 | 0.5 |
| H-Zeolon | 0.5 |
| REY | 0.4 |
| Amorphous Silica-Alumina | 0.6 |
| Erionite | 38 |

It is to be realized that above constraint index values typically characterize the specified solids but that such are the cumulative result of several variables used in determination and calculation thereof. Thus, for a given porous solid depending on the temperature employed within the aforenoted range of 550° F. to 950° F., with accompanying conversion between 10% and 60%, the constraint index may vary within the said approximate range of less than 1. Likewise other variables such as the particle size of the material, the presence of possibly occluded contaminants and binders intimately combined with the same may affect the constraint index. It will accordingly be understood by those skilled in the art that the constraint index, as utilized herein, while affording a highly useful means for characterizing the catalysts of interest is approximate, taking into consideration the manner of its determination, with the probability, in some instances, of compounding variable extremes. However, in all instances, at a temperature within the above-specified range of 550° F. to 950° F., the constraint index will have a value for any given catalyst of interest herein of unity or lower.

The most active forms for the present purpose are those in which cationic sites are occupied at least in part by protons, sometimes called the "acid form." Protons may be introduced by base exchange with ammonium or amine cations and calcination to decompose the ammonium or substituted ammonium cation.

Preferably, the catalyst also includes a metal having hydrogenation capability such as the metals of Group VIII of the Periodic Table, plus chromium, tantalum, tungsten, vanadium, gold and the like which will enhance selectivity to benzene at the higher temperatures of the range contemplated. Preferred metals for this purpose are nickel and cobalt. These metals may be introduced by base exchange or impregnation. In general, the selected metal should be chosen with regard to reaction temperature comtemplated. Platinum can be used at high temperatures above about 800° F. which favors dehydrogenation to benzene rings. At lower temperatures, platinum will result in saturation of rings and destruction of product. Nickel can be used effectively at those lower temperatures.

Temperatures for the catalyst used according to this invention may vary depending upon design factors of the equipment. Generally these lie between 550° F. and 1000° F. Pressures will also be dictated, at least in part, by design factors of the equipment and may vary from 100 to 2000 lb. per square inch gauge.

In general, a temperature will be chosen which suits commercial needs at a particular place and time. It is generally true that higher temperatures tend to increase the yield of benzene. Note particularly the data at different temperatures in Tables 1 and 3, below. Based on these data, it will be clear that a temperature can be chosen to maximize either benzene or xylenes.

In this connection, it is noted again that the temperature of reaction is related to character of the hydrogenation metal, if any, on the catalyst. Many prior art aromatic processing catalysts employ a metal of the platinum group. These are very potent hydrogenation catalysts. At temperatures much below 800° F., hydrogenation of the ring destroys greater amounts of product, the more the temperature is reduced. At the higher temperatures, thermodynamic equilibria favor the benzene ring. The present catalysts are effective with such metals as nickel which give negligible ring hydrogenation at the lower temperatures here possible. In general, it is preferred to use these less potent metal catalysts in this invention to afford temperature flexibility with consequent capability for high throughput.

Suitable space velocities vary from 0.5 to 10 by weight.

The process requires the presence of hydrogen. Preferably, the smallest amount of hydrogen consistent with the desired rate and selectivity of conversion and with adequate catalyst life between regenerations will be selected to minimize the load on compressors, heat exchangers, etc. The hydrogen admixed with charge will generally lie between about 0.5 and 10 mols of hydrogen per mol of hydrocarbon charge.

Severity of the reaction is a function of both temperature and space velocity. Excessive severity will result in undue cracking of the charge. Insufficient severity may permit build up of $C_{10}^+$ aromatics through $C_9^+$ disproportionation-type reactions. Thus, the two factors should be adjusted in relationship to each other. For example, space velocity in the lower part of the claimed range will indicate lower temperatures of reaction, and vice versa.

The nature of the conversion obtained will be apparent from examples presented below.

EXAMPLE 1 & 2

Runs were conducted for reaction of $C_9^+$ reformate over zeolite X which had been base exchanged with a mixture of rare earth chlorides by the technique described in U.S. Pat. No. 3,140,353. Analysis of the charge, reaction conditions and character of product are reported in Table 1.

TABLE 1

| REACTION OF $C_9^+$ AROMATICS OVER REX | | |
|---|---|---|
| Example Number | 1 | 2 |
| Catalyst type | REX | REX |
| Temperature, ° F. | 797.00 | 897.00 |
| Pressure, PSIG | 400.00 | 400.00 |
| WHSV | 2.00 | 2.00 |
| H$_2$/HC | 4/10 | 4/10 |
| Material Balance | 93.86 | 96.30 |
| Time on Stream, Hrs. | 1.00 | 21.20 |
| Product Dist., Wt. % | | |
| C$_1$ | .02 | .00 |
| C$_2$'s | .48 | .57 |
| C$_3$'s | 1.33 | 1.18 |

TABLE 1-continued
REACTION OF $C_9+$ AROMATICS OVER REX

| Example Number | | 1 | 2 |
|---|---|---|---|
| $C_4$'s | | 1.06 | .22 |
| $C_5$'s | | .41 | .07 |
| $C_6$'s | | .38 | .01 |
| Benzene | | 1.14 | 1.23 |
| $C_7$'s | Charge 318–349° F. Cut From Platinum Reformate | .20 | .00 |
| Toluene | | 7.25 | 2.60 |
| $C_8$'s | | .40 | .06 |
| Ethyl Benzene | | .00 | .77 |
| M- + P-xylene | | 5.8 | 18.67 | 
| O-xylene | | 3.7 | 5.76 |
| $C_9+$'s Par. | | 0.6 | .23 |
| $C_9$ Aromatics | | 69.2 | 39.18 |
| $C_{10}$ Aromatics | | 19.4 | 19.14 |
| $C_{11}$–$C_{12}$ Aromatics | | 1.3 | 1.88 |
| | | 100.0 | |
| Naphthalenes | | | .89 |
| $C_{13}+$'s | | | 1.58 |
| Total Wt. % Conv. | | | 30.65 |
| Wt. % Reacted | | | |
| Toluene | | .00 | .00 |
| $C_9$ Aromatics | | 43.39 | 5.64 |
| $C_{10}$ Aromatics | | 1.36 | 14.99 |
| $C_{11}$–$C_{12}$ Aromatics | | 44.50 | 91.80 |
| Wt. % | | | |
| $C_1$–$C_5$ Made | | 3.30 | 2.05 |
| Benzene Made | | 1.14 | 1.23 |
| Xylenes Made | | 14.93 | 1.15 |
| Ring Loss | | 1.10 | .45 |
| $H_2$ Consumed | | .09 | .04 |
| Selectivity | | | |
| $C_1$–$C_5$ Made/Conv. | | 10.76 | 24.42 |
| Benzene Made/Conv. | | 3.71 | 14.72 |
| Xylenes Made/Conv. | | 48.70 | 13.76 |

Corrected row (Example 2 column):
- M- + P-xylene: 7.06
- O-xylene: 3.60
- $C_9+$'s Par.: .33
- $C_9$ Aromatics: 65.29
- $C_{10}$ Aromatics: 16.49
- $C_{11}$–$C_{12}$ Aromatics: .11
- Naphthalenes: .12
- $C_{13}+$'s: .27
- Total Wt. % Conv.: 8.38

EXAMPLES 3 – 6

Runs were conducted with nickel exchanged mordenite, acid zeolite Beta and amorphous silica-alumina of 46 Activity Index. See Table 2.

TABLE 2
REACTION OF $C_9+$ AROMATICS OVER NI-MORDENITE H-BETA, $SiO_2/Al_2O_3$

| Example Number | | 3 | 4 |
|---|---|---|---|
| Catalyst Type | | NI-MORD. | NI-MORD. |
| Temperature ° F. | | 649.00 | 798.00 |
| Pressure, PSIG | | 400.00 | 400.00 |
| WHSV | | 2.00 | 2.00 |
| $H_2$/HC | | 4/10 | 4/10 |
| Material Balance | | 94.23 | 95.23 |
| Time on Stream, Hrs. | | 1.10 | 2.60 |
| Product Dist., Wt. % | | | |
| $C_1$ | | .00 | .40 |
| $C_2$'s | | 1.19 | 4.31 |
| $C_3$'s | | 3.84 | 10.11 |
| $C_4$'s | | 1.56 | 1.90 |
| $C_5$'s | | .53 | .57 |
| $C_6$'s | | .26 | .22 |
| Benzene | | 1.46 | 2.46 |
| $C_7$'s | Charge 318–349° F. | .19 | .05 |
| Toluene | Cut From | 9.08 | 15.38 |
| $C_8$'s | Platinum Reformate | .21 | .24 |
| Ethyl Benzene | | .00 | .00 |
| M- + P-xylene | | 5.8 | 18.14 | 23.36 |
| O-xylene | | 3.7 | 4.58 | 6.92 |
| $C_9+$'s Par. | | 0.6 | .05 | .02 |
| $C_9$ Aromatics | | 69.2 | 42.78 | 26.47 |
| $C_{10}$ Aromatics | | 19.4 | 12.10 | 5.57 |
| $C_{11}$–$C_{12}$ Aromatics | | 1.3 | 1.93 | .80 |
| | | 100.0 | | |
| Naphthalenes | | | 1.18 | .58 |
| $C_{13}+$'s | | | .94 | .64 |
| Total Wt. % Conv. | | | 34.27 | 57.64 |
| Wt. % Reacted | | | | |
| Toluene | | | .00 | .00 |
| $C_9$ Aromatics | | | 38.19 | 61.75 |
| $C_{10}$ Aromatics | | | 37.63 | 71.30 |
| $C_{11}$–$C_{12}$ Aromatics | | | 48.19 | 38.13 |
| Wt. % | | | | |
| $C_1$–$C_5$ Made | | | 7.11 | 17.28 |
| Benzene Made | | | 1.46 | 2.46 |
| Xylenes Made | | | 13.22 | 20.78 |
| Ring Loss | | | .72 | 6.80 |
| $H_2$ Consumed | | | .31 | 1.05 |
| Selectivity | | | | |
| $C_1$–$C_5$ Made/Conv. | | | 20.74 | 29.98 |
| Benzene Made/Conv. | | | 4.27 | 4.27 |
| Xylenes Made/Conv. | | | 38.57 | 36.05 |

| Example Number | | 5 | 6 |
|---|---|---|---|
| Catalyst Type | | H-BETA | $SiO_2/Al_2O_3$ |
| Temperature, ° F. | | 651.00 | 803.00 |
| Pressure, PSIG | | 400.00 | 400.00 |
| WHSV | | 2.00 | 2.00 |
| $H_2$/HC | | 4/10 | 4/10 |
| Material Balance | | 91.34 | 94.05 |
| Time on Stream, Hrs. | | 1.80 | 1.00 |
| Product Dist., Wt. % | | | |
| $C_1$ | | .00 | .00 |
| $C_2$'s | | .10 | .41 |
| $C_3$'s | | 2.01 | 1.04 |
| $C_4$'s | | 1.73 | .91 |
| $C_5$'s | | .83 | .44 |
| $C_6$'s | | .54 | .27 |
| Benzene | | 1.28 | 1.01 |
| $C_7$'s | Charge 318–349° F. | .14 | .17 |
| Toluene | Cut From Platinum Reformate | 10.62 | 5.06 |
| $C_8$'s | | .23 | .23 |
| Ethyl Benzene | | .00 | .00 |
| M- + P-xylene | 5.8 | 21.70 | 15.96 |
| O-xylene | 3.7 | 5.72 | 5.54 |
| $C_9+$'s Par. | 0.6 | .06 | .23 |
| $C_9$ Aromatics | 69.2 | 34.29 | 46.82 |
| $C_{10}$ Aromatics | 19.4 | 14.95 | 18.97 |
| $C_{11}$–$C_{12}$ Aromatics | 1.3 | 2.48 | .47 |
| | 100.0 | | |
| Naphthalenes | | .81 | .00 |
| $C_{13}+$'s | | 2.49 | 2.45 |
| Total Wt. % Conv. | | 39.89 | 24.00 |
| Wt. % Reacted | | | |
| Toluene | | .00 | .00 |
| $C_9$ Aromatics | | 50.44 | 32.34 |
| $C_{10}$ Aromatics | | 22.93 | 2.23 |
| $C_{11}$–$C_{12}$ Aromatics | | 90.54 | 63.67 |
| Wt. % | | | |
| $C_1$–$C_5$ Made | | 4.67 | 2.81 |
| Benzene Made | | 1.28 | 1.01 |
| Xylenes Made | | 17.92 | 12.01 |
| Ring Loss | | 1.81 | .60 |
| $H_2$ Consumed | | .12 | .11 |
| Selectivity | | | |
| $C_1$–$C_5$ Made/Conv. | | 11.70 | 11.70 |
| Benzene Made/Conv. | | 3.22 | 4.22 |
| Xylenes Made/Conv. | | 44.92 | 50.03 |

EXAMPLES 7 – 16

The effect of catalyst aging is shown in Table 3 reporting a series of runs in which the catalyst was acid mordenite plus 1.1% nickel in an alumina binder.

TABLE 3
AGING IN CONVERSION OF $C_9+$ AROMATICS TO BTX OVER NI-MORDENITE

| Example Number | 7 | 8 | 9 |
|---|---|---|---|
| Catalyst Type | Zeolon plus 1.1% Ni, $Al_2O_3$ Binder | | |
| Temperature, ° F. | 748.00 | 750.00 | 749.00 |
| Pressure, PSIG | 400.00 | 400.00 | 400.00 |
| WHSV | 2.00 | 2.00 | 2.00 |
| $H_2$/HC | 4/10 | 4/10 | 4/10 |
| Material Balance | 93.50 | 92.02 | 91.36 |
| Time on Stream, Hrs. | 1.25 | 24.70 | 48.70 |

TABLE 3-continued
AGING IN CONVERSION OF $C_9+$ AROMATICS TO BTX OVER NI-MORDENITE

| Product Dist., Wt. % | | | | |
|---|---|---|---|---|
| $C_1$ | | .15 | .05 | .04 |
| $C_2$'s | | 3.65 | .87 | .45 |
| $C_3$'s | | 9.03 | 4.08 | 2.42 |
| $C_4$'s | | 2.35 | .73 | .52 |
| $C_5$'s | | .66 | .22 | .18 |
| $C_6$'s | | .29 | .16 | .13 |
| Benzene | | 2.22 | 1.57 | 1.28 |
| $C_7$'s | Charge 318–349° F. Cut From Platinum Reformate | .08 | .05 | .04 |
| Toluene | | 14.38 | 4.98 | 3.30 |
| $C_8$'s | | .23 | .09 | .07 |
| Ethyl Benzene | | .00 | .00 | .00 |
| M- + P-xylene | 5.8 | 22.87 | 11.12 | 9.62 |
| O-xylene | 3.7 | 6.71 | 2.89 | 2.78 |
| $C_9+$'s Par. | 0.6 | .00 | .12 | .13 |
| $C_9$ Aromatics | 69.2 | 28.45 | 57.58 | 62.14 |
| $C_{10}$ Aromatics | 19.4 | 6.97 | 13.18 | 15.08 |
| $C_{11}$–$C_{12}$ Aromatics | 1.3 | .74 | 1.21 | .99 |
| | 100.0 | | | |
| Naphthalenes | | .14 | .16 | .24 |
| $C_{13}+$'s | | 1.08 | .93 | .60 |
| Total Wt. % Conv. | | 54.35 | 19.22 | 13.07 |
| Wt. % Reacted | | | | |
| Toluene | | .00 | .00 | .00 |
| $C_9$ Aromatics | | 58.89 | 16.79 | 10.21 |
| $C_{10}$ Aromatics | | 64.08 | 32.05 | 22.25 |
| $C_{11}$–$C_{12}$ Aromatics | | 43.24 | 7.05 | 23.49 |
| Wt. % | | | | |
| $C_1$–$C_5$ Made | | 15.83 | 5.95 | 3.61 |
| Benzene Made | | 2.22 | 1.57 | 1.28 |
| Xylenes Made | | 20.09 | 4.51 | 2.91 |
| Ring Loss | | 6.29 | 2.15 | .71 |
| $H_2$ Consumed | | .95 | .34 | .18 |
| Selectivity | | | | |
| $C_1$–$C_5$ Made/Conv. | | 29.12 | 30.97 | 27.58 |
| Benzene Made/Conv. | | 4.09 | 8.18 | 9.76 |
| Xylenes Made/Conv. | | 36.96 | 23.49 | 22.24 |
| Example Number | | 10 | 11 | 12 |

| | | | | |
|---|---|---|---|---|
| Catalyst Type | | Zeolon plus 1.1% Ni, $Al_2O_3$ Binder | | |
| Temperature, ° F. | | 749.00 | 850.00 | 850.00 |
| Pressure, PSIG | | 400.00 | 400.00 | 400.00 |
| WHSV | | 2.00 | 2.00 | 2.00 |
| $H_2$/HC | | 4/10 | 4/10 | 4/10 |
| Material Balance | | 94.14 | 91.58 | 93.81 |
| Time on Stream, Hrs. | | 72.80 | 96.80 | 191.30 |
| Product Dist., Wt. % | | | | |
| $C_1$ | | .01 | .37 | .13 |
| $C_2$'s | | .37 | 1.68 | 1.02 |
| $C_3$'s | | 2.00 | 2.18 | 1.22 |
| $C_4$'s | | .41 | .52 | .37 |
| $C_5$'s | | .12 | .19 | .11 |
| $C_6$'s | | .10 | .12 | .06 |
| Benzene | | 1.13 | 1.98 | 1.45 |
| $C_7$'s | Charge 318–349° F. Cut From Platinum Reformate | .03 | .04 | .02 |
| Toluene | | 2.76 | 5.81 | 3.18 |
| $C_8$'s | | .02 | .12 | .06 |
| Ethyl Benzene | | .00 | .00 | .00 |
| M- + P-xylene | 5.8 | 9.06 | 11.44 | 9.01 |
| O-xylene | 3.7 | 2.83 | 3.03 | 2.79 |
| $C_9+$'s Par. | 0.6 | .21 | .14 | .21 |
| $C_9$ Aromatics | 69.2 | 63.58 | 58.66 | 64.31 |
| $C_{10}$ Aromatics | 19.4 | 16.42 | 12.56 | 14.81 |
| $C_{11}$–$C_{12}$ Aromatics | 1.3 | .36 | .11 | .66 |
| | 100.0 | | | |
| Naphthalenes | | .03 | .11 | .07 |
| $C_{13}+$'s | | .56 | .95 | .53 |
| Total Wt. % Conv. | | 10.79 | 19.70 | 11.43 |
| Wt. % Reacted | | | | |
| Toluene | | .00 | .00 | .00 |
| $C_9$ Aromatics | | 8.12 | 15.23 | 7.07 |
| $C_{10}$ Aromatics | | 15.34 | 35.25 | 23.68 |
| $C_{11}$–$C_{12}$ Aromatics | | 72.30 | 91.52 | 48.90 |
| Wt. % | | | | |
| $C_1$–$C_5$ Made | | 2.90 | 4.95 | 2.85 |
| Benzene Made | | 1.13 | 1.98 | 1.45 |
| Xylenes Made | | 2.39 | 4.97 | 2.29 |
| Ring Loss | | .45 | .34 | .06 |
| $H_2$ Consumed | | .14 | .27 | .13 |
| Selectivity | | | | |
| $C_1$–$C_5$ Made/Conv. | | 26.91 | 25.11 | 24.92 |
| Benzene Made/Conv. | | 10.45 | 10.04 | 12.71 |
| Xylenes Made/Conv. | | 22.12 | 25.24 | 20.07 |
| Example Number | 13 | 14 | 15 | 16 |

| | | | | |
|---|---|---|---|---|
| Catalyst Type | | Zeolon plus 1.1% Ni, $Al_2O_3$ Binder | | |
| Temperature, ° F. | 850.00 | 849.00 | 850.00 | 850.00 |
| Pressure, PSIG | 400.00 | 400.00 | 400.00 | 410.00 |

TABLE 3-continued
AGING IN CONVERSION OF $C_9+$ AROMATICS TO BTX OVER NI-MORDENITE

| | | | | | |
|---|---|---|---|---|---|
| WHSV | | 2.00 | 2.00 | 2.00 | 2.00 |
| $H_2$/HC | | 4/10 | 4/10 | 4/10 | 4/10 |
| Material Balance | | 95.10 | 95.05 | 96.30 | 80.22 |
| Time on Stream, Hrs. | | 216.65 | 239.30 | 263.30 | 335.30 |
| Product Dist., Wt. % | | | | | |
| $C_1$ | | .11 | .08 | .06 | .30 |
| $C_2$'s | | .91 | .84 | .95 | 4.69 |
| $C_3$'s | | 1.01 | 1.01 | 1.21 | 4.55 |
| $C_4$'s | | .32 | .38 | .39 | 1.18 |
| $C_5$'s | | .08 | .08 | .08 | .07 |
| $C_6$'s | | .05 | .06 | .06 | .06 |
| Benzene | | 1.36 | 1.34 | 1.32 | 1.56 |
| $C_7$'s | Charge | .03 | .01 | .02 | .01 |
| | 318–349° F. | | | | |
| Toluene | Cut From | 2.97 | 2.82 | 2.72 | 2.57 |
| $C_8$'s | Platinum | .06 | .06 | .02 | .17 |
| | Reformate | | | | |
| Ethyl Benzene | | .00 | .00 | .00 | .00 |
| M- + P-xylene | 5.8 | 8.82 | 8.68 | 8.59 | 7.67 |
| O-xylene | 3.7 | 2.82 | 2.85 | 2.84 | 2.59 |
| $C_9+$'s Par. | 0.6 | .16 | .16 | .19 | .15 |
| $C_9$ Aromatics | 69.2 | 64.88 | 65.15 | 65.08 | 59.44 |
| $C_{10}$ Aromatics | 19.4 | 15.19 | 15.75 | 15.33 | 14.39 |
| $C_{11}$-$C_{12}$ Aromatics | 1.3 | .64 | .16 | .61 | .13 |
| | 100.0 | | | | |
| Naphthalenes | | .05 | .06 | .04 | .06 |
| $C_{13}+$'s | | .53 | .50 | .50 | .39 |
| Total Wt. % Conv. | | 10.51 | 10.14 | 10.15 | 17.50 |
| Wt. % Reacted | | | | | |
| Toluene | | .00 | .00 | .00 | .00 |
| $C_9$ Aromatics | | 6.24 | 5.85 | 5.95 | 14.10 |
| $C_{10}$ Aromatics | | 21.72 | 18.83 | 20.99 | 25.84 |
| $C_{11}$-$C_{12}$ Aromatics | | 50.43 | 87.65 | 53.25 | 89.94 |
| Wt. % | | | | | |
| $C_1$-$C_5$ Made | | 2.44 | 2.39 | 2.69 | 10.80 |
| Benzene Made | | 1.36 | 1.34 | 1.32 | 1.56 |
| Xylenes Made | | 2.14 | 2.03 | 1.92 | .77 |
| Ring Loss | | .34 | .37 | .04 | 8.24 |
| $H_2$ Consumed | | .10 | .10 | .13 | .87 |
| Selectivity | | | | | |
| $C_1$-$C_5$ Made/Conv. | | 23.20 | 23.56 | 26.46 | 61.70 |
| Benzene Made/Conv. | | 12.96 | 13.22 | 13.01 | 8.94 |
| Xylenes Made/Conv. | | 20.38 | 20.04 | 18.96 | 4.39 |

It is to be noted that the higher xylene content of the charge the lower the net xylene production. In fact, if the xylene content of the charge exceeds 30 – 35%, there may be a net loss of xylene.

It will be seen that the present invention provides a means for manufacture of xylenes from reformate without the expensive extraction step usually practiced and with conservation of xylenes in the reformate for use in motor gasoline.

COMMERCIAL EMBODIMENTS

The drawings illustrate advantageous process arrangements for applying the present invention to good advantage. As shown in FIG. 1, a full range naphtha is charged to a platinum reformer 10, where it is processed under conditions usual in the art. The full range reformate is transferred by line 11 to a distillation column 12 operated to take most of the $C_8$ and lighter fraction overhead by line 13 and to provide a bottoms fraction of $C_9+$ with only minor amounts of $C_8$, depending upon efficiency of the fractionation available. The $C_9+$ reformate passes by line 14 to a reactor 15 for practice of the present invention. Hydrogen is added to the charge from hydrogen recycle line 16 with addition of such make up hydrogen as may be needed at line 16. The converted product passes from a high pressure separator 17 from which excess hydrogen is taken overhead by line 16 for recycle in the process.

The liquid product, together with lower boiling material other than methane passes to fractionator 18 from which light hydrocarbons are taken overhead as gas at line 19 and benzene is removed as a side stream at line 20. The bottoms from fractionator 18, constituted almost entirely by aromatics boiling above benzene passes by line 21 to a fractionator 22. Toluene is taken overhead from column 22 by line 23 and the $C_8+$ aromatics are withdrawn as bottoms by line 24. The bottoms from column 22 are thus transferred to a fractionator 25 from which a $C_8$ aromatics stream is taken overhead for processing to desired chemicals. The bottoms of column 25 are constituted by $C_9+$ aromatics which can be recycled in the process by line 26. As shown above, it is advantageous to recycle the toluene from line 23 and the $C_9+$ fraction from line 26 back to charge of reactor 15.

Very little naphthalene has been found in the products of this reaction. If naphthalenes are introduced to the system, buildup can be prevented by taking a drag stream of column 25 bottoms through line 27.

The embodiment shown in FIG. 1 is ideally suited to an operation in which high quality gasoline meeting the needs of today's environmental restrictions can be prepared while still manufacturing BTX.

It will be apparent that the $C_8^-$ fraction taken overhead from fractionator 12 by line 13 is a low boiling fraction of high octane number which is advantageously employed for blending with other motor fuel components (catalytic gasoline, straight run gasoline, alkylate, additives and the like) to prepare a finished motor gasoline. The $C_9+$ product taken as bottoms from fractionator 25 is also a splendid motor fuel component which may be passed from line 27 to gasoline blending. This $C_9+$ product fraction has higher volatility than the $C_9+$ charge prepared by fractionator 12 and is used to advantage for motor fuel, in whole or part, depending upon the need to prepare BTX. The integration of the process of this invention is thus seen to afford a remarkably high degree of flexibility to a refinery/chemical manufacturing complex.

Figure 2:
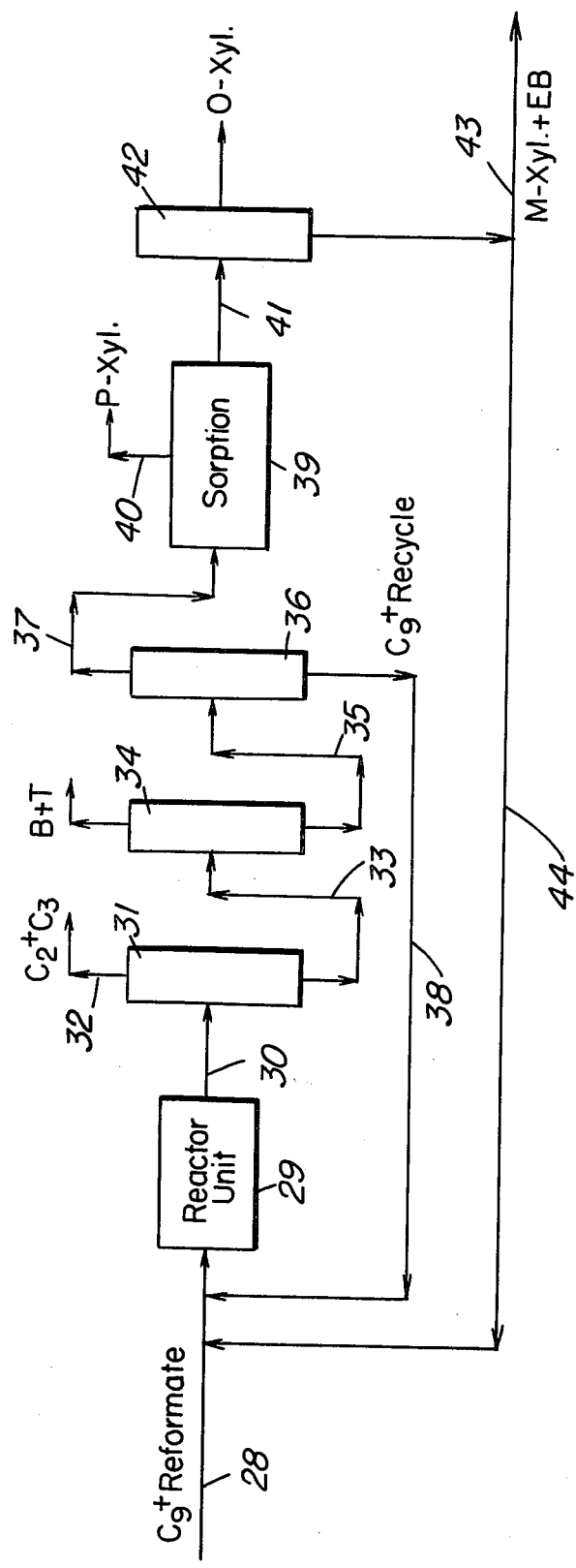
FIG. 2 is a flow sheet of processing $C_9^+$ reformate to manufacture BTX in which advantage is taken of isomerization activity of the catalyst.

The catalyst used according to this invention is very effective is isomerization of $C_8$ aromatics. It thus becomes possible to include the reactor of this invention in the recovery loop for manufacture of paraxylene and alternatively orthoxylene. Such an arrangement is shown in FIG. 2 where a $C_9^+$ reformate is supplied by line 28. That heavy reformate is prepared in a manner similar to the distillation in column 12 of FIG. 1. The heavy reformate passes to a reactor 29 here shown as a single process block. It will be understood that the reactor unit includes the auxiliary shown in FIG. 1 together with heat exchangers, compressors and other equipment necessary to accomplish the result. The effluent of reactor 29 passes by line 30 to a fractionator 31 from which light aliphatic components are taken overhead at line 32. The bottoms pass by line 33 to column 34 from which benzene and toluene are taken overhead and the bottoms passed by line 35 to a fractionator 36. A xylene fraction is taken overhead from column 36 by line 37 and a $C_9^+$ recycle passes by line 38 back to the reactor charge.

The xylene fraction from line 37 is subjected to an operation for separation of paraxylene at 39. This may be either fractional crystallization or selective sorption as known in the art. Product p-xylene is recovered by line 40. The remaining xylenes pass by line 41 to a column 42 where orthoxylene is separated by fractional distillation.

The bottoms of column 42 are constituted by $C_8$ aromatics lean in p-xylene and o-xylene and are therefore mainly m-xylene and ethyl benzene. Those bottoms may be withdrawn by line 43 for any desired purposes but are preferably recycled in the system by line 44 to reactor 29. In reactor 29, the meta xylene is isomerized to produce additional p-xylene and o-xylene.

The results of operating such a system in different manners can be calculated. The manner of modifying the flow sheet of FIG. 2 will be apparent to one skilled in the art in order to provide the cases shown in Table 4 below:

end point which avoids introduction of $C_9$ or heavier aromatics.

The light naphtha is reformed in platinum reformer 45 to dehydrogenate the naphthenes to aromatics. The reformate is fractionated in column 46 and the material boiling below about 150° F. is taken overhead to provide a bottoms fraction boiling between 150°–300° F. That material is charged to a solvent extraction unit 47 wherein aromatics are separated from the aliphatic compounds. The extraction is reasonably efficient but does leave some non-aromatics in the extract which is transferred by line 48 to distillation for separation into benzene, toluene and $C_8$ aromatics. The xylenes are recovered from the latter by the known techniques of selective sorption or fractional crystallization with isomerization of the material from which a desired xylene has been separated. The $C_8$ fraction of the material withdrawn by line 48 normally contains about 15 to 18% of ethyl benzene, a troublesome component in xylene separations. This should be contrasted with the low levels of ethyl benzene reported above for operation in accordance with this invention.

Figure 3A:
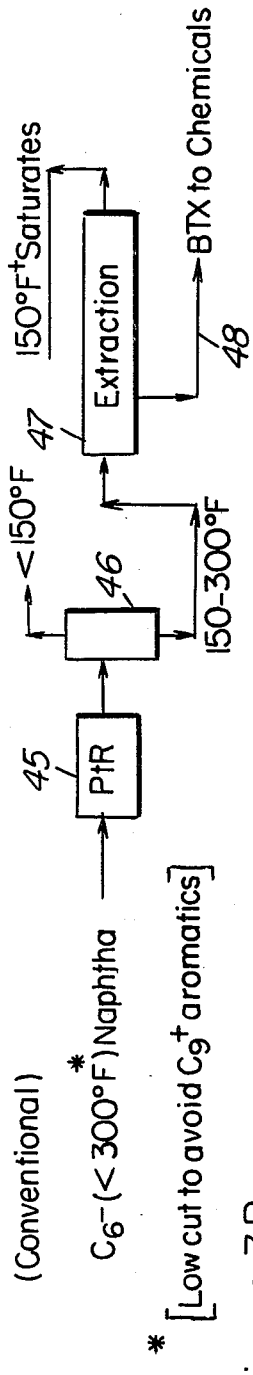
FIG. 3 is constituted by three flow sheets for comparative purposes.
Figure 3B:
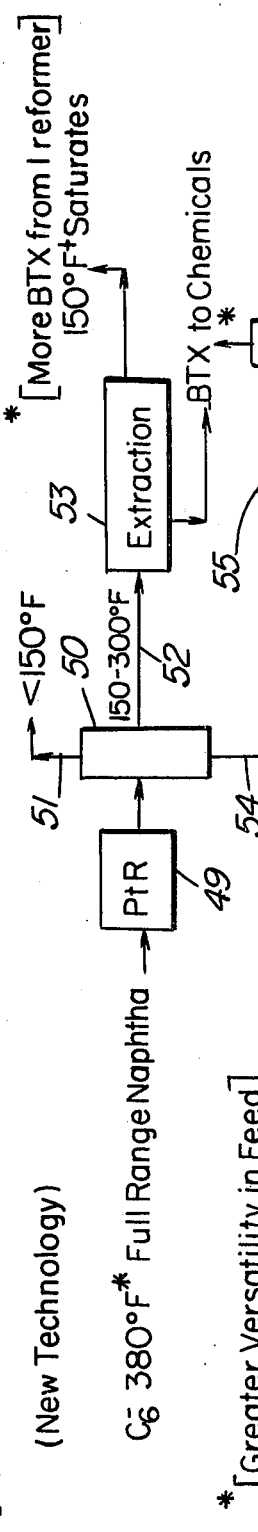

FIG. 3B utilizes the new technology provided by this invention in a system to increase the amount of BTX derived from operation of a single reformer. In this case, full range naphtha is charged to platinum reformer 49. The reformate is fractionated in column 50 to separate a light overhead in line 51 comprised mainly by non aromatic hydrocarbons. A light aromatic reformate boiling between 130° and 300° F. is transferred by fractionator 50 by line 52 and subjected to solvent extraction in extractor 53. The extracted aromatics are handled in the same manner as in FIG. 3A. The heavy reformate, boiling above about 300° F. is transferred by line 54 to reactor 55 in which it is converted in the manner described hereinabove to generate additional BTX. The product is fractionated in a system indicated generally by 56 and unreacted heavier aromatics are recycled by line 57.

Figure 3C:
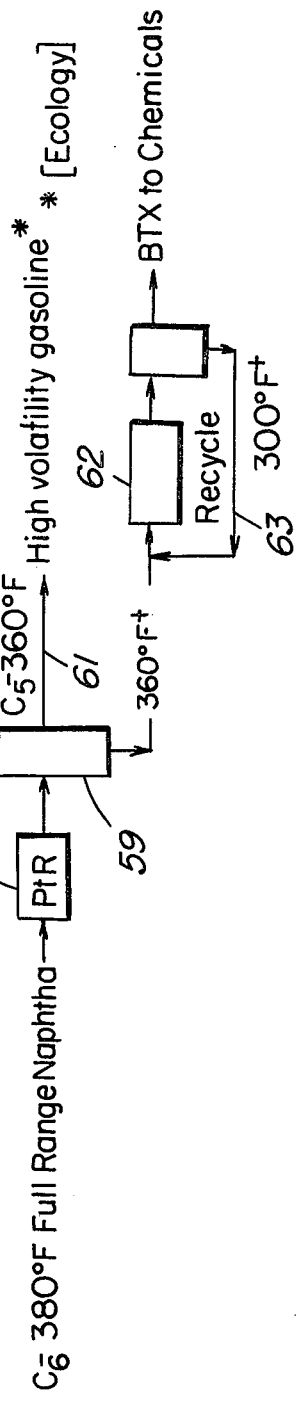

The flow sheet of FIG. 3C illustrates the preferred embodiment of this invention in which the high volatility reformate containing BTX formed during reforming is utilized to best advantage in manufacture of gasoline.

TABLE 4

| | PRODUCT YIELDS FROM VARIANTS OF FIGURE 2 (PARTS BY WEIGHT) | | | | | | |
|---|---|---|---|---|---|---|---|
| | $C_9^+$ Reformate | $C_2 + C_3$ | B + T | $C_9^+$ Recycle | p-xylene | m-xylene + EB | o-xylene |
| CASE A | | | | | | | |
| No xylene recycle | 68 | 14 | 23 | 32 | 7 | 16 | 7 |
| CASE B | | | | | | | |
| o- and p-xylene recovered, balance recycled | 37 | 7 | 16 | 47 | 7 | 16 | 7 |
| CASE C | | | | | | | |
| p-xylene recovered, balance recycled | 19 | 4 | 8 | 58 | 7 | 16 | 7 |

The three flow sheets of FIG. 3 provide graphical comparisons of conventional manufacture of BTX from reformate with two alternative approaches to commercial application of the present invention. FIG. 3A represents the process scheme now widely followed in commercial production of BTX. A light naphtha which includes the $C_6$ hydrocarbons of the distillate from crude and having an end point less than 300° F. is subjected to catalytic reforming. The naphtha is cut at an The full range naphtha reformed in reformer 58 passes to fractionator 59. Light hydrocarbons, are taken overhead by line 60 to be used for pressuring gasoline, bottled gas and the like. The $C_5$-360° F. fraction is a highly aromatic gasoline blending stock of relatively low boiling point, desirable for making high volatility, high front end octane number gasoline. This fraction passes by line 61 to gasoline blending facilities. The heavy end of the reformate (360° F.+) is reacted in converter 62 in accordance with the present invention to manufacture BTX. The 300° F.+ product is recycled by line 63.

We claim:

1. In the manufacture of gasoline and concurrent production of chemical grade aromatic compounds of eight or less carbon atoms by catalytic reforming of naphtha and using part of the reformate for each purpose, the improvement resulting in higher quality gasoline of lower "heavy end" content, which comprises fractionating a catalytic reformate to provide a light reformate containing most of the $C_8$ and lighter components of the reformate and a heavy reformate which contains no more than 20 weight percent of xylenes, blending said light reformate with other motor fuel components to provide a finished gasoline, contacting said heavy reformate with a solid, porous, acid catalyst characterized by a constraint index not higher than 1 at about 550° to about 1000° F., about 100 to about 2000 pounds per square inch, admixed with 0.5 to 10 mols of hydrogen per mol of hydrocarbon and at a weight hourly space velocity between about 0.1 and about 200 unit weights of hydrocarbon per unit weight of said catalyst per hour, and recover at least one aromatic compound of eight or less carbon atoms from the product of contacting said heavy reformate with said catalyst.

2. The process of claim 1 wherein said heavy reformate charge includes a minor amount of eight carbon atom aromatics and is essentially free of aromatics having less than eight carbon atoms.

3. The process of claim 1 wherein the operating conditions range from about 0.5 to 10 WHSV.

4. The process of claim 1 wherein said catalyst includes a hydrogenation metal.

5. The process of claim 4 wherein said metal is nickel.

6. The process of claim 4 wherein said metal is nickel or cobalt.

7. A process for producing aromatic compounds of six to eight carbon atoms from an aromatic hydrocarbon charge predominantly higher in molecular weight than eight carbon atom aromatics, without substantial formation of heavier (350° F.+) aromatics through conventional disproportionation or transalkylation reactions, which process comprises contacting said charge with a porous solid acid catalyst characterized by a constraint index not higher than 1 at about 550 to about 1000° F., about 100 to about 2,000 pounds per square inch, admixed with 0.5 to 10 mols of hydrogen per mol of hydrocarbon and at a weight hourly space velocity between about 0.1 and about 200 unit weights of hydrocarbon per unit weight of said catalyst per hour and recovering at least one aromatic compound of eight or less carbon atoms from the product of contacting said charge with said catalyst.

8. The process of claim 7 wherein said charge includes a minor amount of eight carbon atom aromatics and is essentially free of aromatics having less than eight carbon atoms.

9. The process of claim 7 wherein said charge is a heavy reformate.

10. The process of claim 7 wherein said charge is a heavy pyrolysis gasoline.

11. The process of claim 7 wherein the operating condition range is from 0.5 to 10 WHSV.

12. The process of claim 7 wherein said catalyst includes a hydrogenation metal.

13. The process of claim 12 wherein said metal is nickel or cobalt.

14. The process of claim 1 wherein $C_9+$ aromatics are separated from said product and admixed with said heavy reformate for contact with such catalyst.

15. The process of claim 1 wherein $C_9+$ aromatics and toluene are separated from said product and admixed with said heavy reformate for contact with said catalyst.

16. The process of claim 1 wherein said heavy reformate contains no more than 10 weight percent of xylenes.

17. The process of claim 7 wherein $C_9+$ aromatics are separated from said product and admixed with said charge for contact with said catalyst.

18. The process of claim 7 wherein $C_9+$ aromatics and toluene are separated from said product and admixed with said charge for contact with said catalyst.

19. The process of claim 7 wherein said charge contains no more than 10 weight percent of xylenes.

20. The process of claim 1 wherein a xylene fraction is separated from said product, a desired xylene isomer is isolated from xylene fraction and the resultant mixture of xylenes lean in said desired isomer is recycled to contact with said catalyst in admixture with said heavy reformate.

21. The process of claim 7 wherein a xylene fraction is separated from said product, a desired xylene isomer is isolated from said xylene fraction, and the resultant mixture of xylenes lean in said desired isomer is recycled to contact with said catalyst in admixture with said charge.

22. The process of claim 1 wherein at least a portion of the said product after recovery therefrom of aromatics of eight or less carbon atoms is blended with other motor fuel components to make a motor gasoline.

* * * * *